United States Patent [19]
Low et al.

[11] Patent Number: 5,820,847
[45] Date of Patent: Oct. 13, 1998

[54] METHOD FOR TARGETING A DIAGNOSTIC AGENT TO CELLS

[75] Inventors: Philip Stewart Low; Mark Alan Horn; Peter Frederick Heinstein, all of West Lafayette, Ind.

[73] Assignee: Purdue Research Foundation, West Lafayettte, Ind.

[21] Appl. No.: 784,019

[22] Filed: Jan. 15, 1997

Related U.S. Application Data

[62] Division of Ser. No. 349,407, Dec. 5, 1994, Pat. No. 5,635,382, which is a division of Ser. No. 851,544, Mar. 13, 1992, Pat. No. 5,416,016, and Ser. No. 498,762, Mar. 28, 1990, Pat. No. 5,108,921, which is a continuation-in-part of Ser. No. 331,816, Apr. 3, 1989, abandoned.

[51] Int. Cl.$^6$ .......................... A61K 49/00; A61K 51/02; A61K 9/127; C12N 15/09
[52] U.S. Cl. ..................... 424/9.1; 424/450; 435/172.3; 435/320.1; 435/325; 436/501; 514/2; 514/44; 935/52; 935/54
[58] Field of Search .................................. 435/325, 410, 435/172.3, 328.1, 320.1; 514/2, 44, 23, 12–19; 935/52, 54; 424/9.1, 450; 436/501

[56] References Cited

U.S. PATENT DOCUMENTS

| 4,136,159 | 1/1979 | Stone ....................................... 424/1.53 |
| 5,416,016 | 5/1995 | Low et al. ............................... 435/325 |

FOREIGN PATENT DOCUMENTS

| 220030 | 4/1987 | European Pat. Off. . |
| 273085 | 7/1988 | European Pat. Off. . |
| 359347 | 8/1988 | European Pat. Off. . |

OTHER PUBLICATIONS

A. Antony, et al., "Studies Of The Role Of A Particulate Folate–Binding Protein In The Uptake Of 5–Methyltetrahydrofolate by Cultured Human KB Cells", The Journal of Biological Chemistry, vol. 260, No. 28, Dec. 5, 1985.

H. Said, "A Carrier–Mediated System For Transport Of Biotin In Rat Intestine In Vitro", Chem Abstracts, vol. 106: 99880d, 1987.

T. Wileman et al., "Receptor–Mediated Endocytosis", Biochem. J. (1985) 232, 1–14.

R. Fallon et al., "Receptor–Mediated Endocytosis and Target Drug Delivery", Hepatology vol. 5, No. 5 pp. 899–901 (1985).

G. Wu et al., "Receptor–Mediated Gene Delivery and Expression in Vivo", The Journal of Biological Chemistry, vol. 263, No. 29, pp. 14621–14624, Oct. 15, 1988.

R. Bennett et al., "DNA Binding to Human Leukocytes", J. Clin. Invest. vol. 76, Dec. 1985, pp. 2182–2190.

O.V. Tubetskaya et al., "Monoclonal Antibody to Human Endothelial Cell Surface Internalization and Liposome Delivery in Cell Culture", Elsevier Science Publishers B.V., vol. 228, No. 1, 131–134, Feb. 1988.

D. Vesely et al., "Isolation of Biotin Receptor from Hepatic Plasma Membranes" Biochemical and Biophysical Research Communications, vol. 143, No. 3, 1987.

R. Morris et al., "Visualization of Intercellular Trafficking: Use of Biotinylated Ligands in Conjunction with Avidin–Gold Colloids", The Journal of Histochemistry and Cytochemistry, vol. 32, No. 1, pp. 124–128, 1984.

L. Chalifour et al., "The Characterization of the Uptake of Avidin–Biotin Complex by HeLa Cells", Biochimica et Biophysical Acta, 721, (1982), pp. 64–69.

B. Kamen et al., "Delivery of Folates to the Cytoplasm of MA104 Cells Is Mediated by a Surface Membrane Receptor That Recycles", The Journal of Biological Chemistry, vol. 263, No. 27, Sep. 25, 1988, pp. 13602–13609.

I. Pastan et al., "Receptor–Mediated Endocytosis of Hormones in Cultured Cells", Ann. Rev. Physiol (1981), vol. 43, pp. 239–50.

E. Bayer et al., "The Use of the Avidin–Biotin Complex as a Tool in Molecular Biology", Methods of Biochemical Analysis, vol. 26 (1979).

H. Said et al., "Biotin Transport in the Human Intestine: Inhibition by Anticonvulsant Drugs", Am. J. Clin. Nutr (1989) vol. 49, pp. 127–31.

E. Bayer et al., "On the Mode of Liposome–Cell Interactions Biotin–Conugated lipids as Ultrastructural Probes", Biochimica et Biophysical Acta, 550 (1979) pp. 464–473.

H. Said et al., "Biotin Transport in Rat Intestinal Brush–Border Membrane Vesicles", Biochimica et Biophysical Acta, 945 (1988) pp. 195–201.

G. Gabor et al., "Biotin–Labelled DNA: A Novel Approach for the Recognition of a DNA Binding Site on Cell Membranes", Biochem. and Biophysical Research Communication, vol. 122, No. 3, Aug. 16, 1984.

R. Blankenburg et al., Interaction between Biotin Lipids and Streptavidin in Monolayers: Formation of Oriented Two–Dimensional Protein Domains Induced by Surface Recoginition:, Biochem, vol. 28, No. 20 (1989).

S. Li et al., "Thiamine Mutants of the Crucifer, Arabidopsis", Biochem. Genetics 3: 163–170 (1969).

G. Russell–Jones et al., Vitamin B12: A Novel Carrier for Orally Presented Antigens: (1988).

R. Blakley et al., "Kinetic Studies of the Reaction Mechanism of Dihydrofolate Reductase", Annals New York Academy of Sciences (1971).

(List continued on next page.)

*Primary Examiner*—Jasemine C. Chambers
*Assistant Examiner*—Scott D. Priebe
*Attorney, Agent, or Firm*—Barnes & Thornburg

[57] ABSTRACT

A method is provided for targeting a diagnostic agent for delivery to a folate receptor-bearing cell of an animal. The method comprises the step of administering to an animal a composition comprising a diagnostic agent complexed with a targeting ligand selected from the group consisting of folate, folate receptor-binding analogs of folate, or other folate receptor-binding ligands.

10 Claims, No Drawings

OTHER PUBLICATIONS

P. T. Condit, M.D., Ph.D., "Discussion Paper: Number of Binding Sites and Possible Mechanisms of Action", Annals of New York Academy of Sciences (1971).

P. Elwood, "Molecular Cloning and Characterization of the Human Folate–binding Protein cDNA from Placenta and Malignant Tissue Culture (KB) Cells", The Journal of Biolog. Chem., vol. 264, No. 25, Sep. 5, 1989, 14893–14901.

G. Hitchings, Ph. D., "Folate Antagonists as Antibacterial and Antiprotozoal Agents", Annals New York Academy of Sciences (1971).

J. Beck et al., "Affinity Labeling of the Folate Methotrexate Transporter from Leishmania donovani", Biochemistry (1989), vol. 28, pp. 6931–6937.

G. Henderson et al., "Affinity Labeling of the 5–Methyltetrahyddrofolate/Methotrexate Transport Protein of L1210 Cells by Treatment with an N–Hydroxy succinimide Ester of [$^3$H] methotrexate," The Journal of Biolog. Chem., vol. 259, No. 7, Apr. 10, 1984, pp. 4558–4562.

S. Jacobs et al., "Discussion Paper: Some Biological and Pharmocologic Properties of Amethopterin–Albumin", Annals New York Academy of Science (1971).

E. Price et al., "Characterization of the Methotrexate Transport Pathway in Murine L1210 Leukemia Cells: Involvement of a Membrane Receptor and a Cytosolic Protein", Biochem (1988) vol. 27, pp. 7853–7858.

B. Shane et al. "Transport and Utilization of Methyltetrahydrofolates by Lactobacillus casei", The Journal of Biolog. Chem., vol. 251, No. 11, Jun. 10, 1976, pp. 3405–3410.

H. Kumar et al., "Folate Transport in Lactobacillus salivarius", The Journal of Biolog. Chem., vol. 262, No. 15, May 25, 1987, pp. 7171–7179.

K. Rothberg, "The Glycophospholipid–linked Folate Receptor Internalizes Folate without Entering the Cathrin–coated Pit Endocytic Pathway", The Journal of Cell Biology, vol. 110, pp. 637–649, Mar. 1990.

I. Goldman, "The Characteristics of the membrane Transport of Amethopterin and the Naturally Occuring Folates", Annals New York Academy of Sciences (1981).

W.S. Bloom, M.D., Ph.D. et al., "Receptor–mediated Endocytosis: Review and Overview", The Mount Sinai Journal of Medicine, vol. 48, No. 5, Sep.–Oct., 1981.

G. Wu et al., "Receptor–medicated in Vitro Gene Transformation by a soluble DNA Carrier System", The Journal of Biology Chemistry, vol. 262, No. 10, Apr. 5, 1987, pp. 4429–4432.

J. Starling et al., "Development of a Dual Lable Fluorescence Technique that Can be Utilized to Elucidate the Mechanism of Action of Monoclonal Antibody–Drug Conjugates", Cancer Research 48, 6211–6216, Nov. 1, 1988.

F. Fox et al., "Nicotinic Acid Active Transport by In Vitro Bullfrog Intestine", Biochimica et Biophysica Acta., 332 (1974) pp. 336–340.

Boumendil–Podevin, et al., Biological Abstracts, 72(4):2967, "Nicotinic Acid Transport by Brush Border Membrane Vesicles From Rabbit Kidney".

Mayhew, et al.; in Liposomes; Ostro (Editor) Marcel Dekker, Inc., New York & Basel; 1983; pp. 289–341.

J. Whiteley, Ph.D., "Some Aspects of the Chemistry of the Folate Molecule", Annals New York Academy of Sciences, (1972).

METHOD FOR TARGETING A DIAGNOSTIC AGENT TO CELLS

CROSS REFERENCE TO RELATED APPLICATIONS

This is a division of application Ser. No. 08/349,407 filed Dec. 5, 1994, now U.S. Pat. No. 5,635,382 issued Jun. 3, 1997, which is a division of application Ser. No. 07/851,544 filed Mar. 13, 1992, now U.S. Pat. No. 5,416,016 issued May 16, 1995 which is a division of application Ser. No. 07/498,762 filed Mar. 28, 1990, now U.S. Pat. No. 5,108,921 issued Apr. 28, 1992, which is a continuation-in-part of application Ser. No. 07/331,816 filed Apr. 3, 1989, now abandoned.

This invention was made with Government support under Grant 89-45-DCB-88-11465, awarded by the National Science Foundation. The Government has certain rights in the invention.

FIELD OF THE INVENTION

This invention relates to a method for enhancing transmembrane transport of exogenous molecules. More particularly, the use of nutrient receptors, including biotin or folate receptors, and the respective associated receptor mediated endocytotic mechanism associated with such receptors, is utilized to enhance the efficiency of cellular uptake of exogenous molecules capable of modulating or otherwise modifying cell function.

BACKGROUND AND SUMMARY OF THE INVENTION

Transmembrane transport of nutrient molecules is a critical cellular function. Because practitioners have recognized the importance of transmembrane transport to many areas of medical and biological science, including drug therapy and gene transfer, there has been significant research efforts directed to the understanding and application of such processes. Thus, for example, transmembrane delivery of nucleic acids has been encouraged through the use of protein carriers, antibody carriers, liposomal delivery systems, electroporation, direct injection, cell fusion, viral carriers, osmotic shock, and calcium-phosphate mediated transformation. However, many of those techniques are limited both by the types of cells in which transmembrane transport is enabled and by the conditions of use for successful transmembrane transport of exogenous molecular species. Further, many of these known techniques are limited in the type and size of exogenous molecule that can be transported across a membrane without loss of bioactivity.

One method for transmembrane delivery of exogenous molecules having a wide applicability is based on the mechanism of receptor mediated endocytotic activity. Unlike many other methods, receptor mediated endocytotic activity can be used successfully both in vivo and in vitro. Receptor mediated endocytosis involves the movement of ligands bound to membrane receptors into the interior of an area bounded by the membrane through invagination of the membrane. The process is initiated or activated by the binding of a receptor specific ligand to the receptor. Many receptor mediated endocytotic systems have been characterized, including those recognizing galactose, mannose, mannose 6-phosphate, transferrin, asialoglycoprotein, transcobalamin (vitamin $B_{12}$), α-2 macroglobulins, insulin, and other peptide growth factors such as epidermal growth factor (EGF).

Receptor mediated endocytotic activity has been utilized for delivering exogenous molecules such as proteins and nucleic acids to cells. Generally, a specified ligand is chemically conjugated by covalent, ionic or hydrogen bonding to an exogenous molecule of interest, (i.e., the exogenous compound) forming a conjugate molecule having a moiety (the ligand portion) that is still recognized in the conjugate by a target receptor. Using this technique the phototoxic protein psoralen has been conjugated to insulin and internalized by the insulin receptor endocytotic pathway (Gasparro, *Biochem. Biophys. Res. Comm.* 141(2), pp. 502–509, Dec. 15, 1986); the hepatocyte specific receptor for galactose terminal asialoglycoproteins has been utilized for the hepatocyte-specific transmembrane delivery of asialoorosomucoid-poly-L-lysine non-covalently complexed to a DNA plasmid (Wu, G. Y., *J. Biol. Chem.*, 262(10), pp. 4429–4432, 1987); the cell receptor for epidermal growth factor has been utilized to deliver polynucleotides covalently linked to EGF to the cell interior (Myers, European Patent Application 86810614.7, published Jun. 6, 1988); the intestinally situated cellular receptor for the organometallic vitamin $B_{12}$-intrinsic factor complex has been used to mediate delivery to the circulatory system of a vertebrate host a drug, hormone, bioactive peptide or immunogen complexed with vitamin $B_{12}$ and delivered to the intestine through oral Admininistration (Russell-Jones et al., European patent Application 86307849.9, published Apr. 29, 1987); the mannose-6-phosphate receptor has been used to deliver low density lipoproteins to cells (Murray, G. J. and Neville, D. M., Jr., *J.Bio.Chem*, Vol. 255 (24), pp. 1194–11948, 1980); the cholera toxin binding subunit receptor has been used to deliver insulin to cells lacking insulin receptors (Roth and Maddox, *J.Cell.Phys.* Vol. 115, p. 151, 1983); and the human chorionic gonadotropin receptor has been employed to deliver a ricin a-chain coupled to HCG to cells with the appropriate HCG receptor in order to kill the cells (Oeltmann and Heath, *J.Biol.Chem*, vol. 254, p. 1028 (1979)).

The method of the present invention enhances the transmembrane transport of an exogenous molecule across a membrane having biotin or folate receptors that initiate transmembrane transport of receptor bound species. The method takes advantage of (1) the location and multiplicity of biotin and folate receptors on the membrane surfaces of most cells and (2) the associated receptor mediated transmembrane processes. Performance of the method involves formation of a complex between a ligand selected from biotin or other biotin receptor-binding compounds, and/or folic acid or other folate receptor-binding compounds, and an exogenous molecule. A cell membrane bearing biotin or folate receptors is contacted with this complex, thereby initiating receptor mediated transmembrane transport of the complex. The complex is allowed to contact the membrane surface bearing the corresponding receptors for a time sufficient to initiate and permit transmembrane transport of the complex. The transmembrane transport of exogenous molecules including proteins and polynucleotides has been promoted in plant, mammalian, and bacterial cells.

In one embodiment of this invention, the target receptor for the method of the present invention is the biotin receptor. Biotin is a necessary cellular nutrient that has been found to be preferentially bound by biotin receptor proteins associated with cellular membranes. Commercially available reagents are used to form a covalent complex between biotin and polynucleotides, proteins, or other desired exogenous molecules. According to one preferred embodiment of the present invention, a biotin/exogenous molecule complex is brought into contact with a membrane having associated biotin receptors for a time sufficient to allow binding of the biotin moiety of the complex to a corresponding biotin receptor in the membrane. This binding triggers the initiation of cellular processes that result in transmembrane transport of the complex.

In an alternate but equally preferred embodiment of this invention, folate receptors are targeted to enhance cellular uptake of exogenous molecules. Folate binding receptors are found in most types of cells, and they have been demonstrated to bind and trigger cellular internalization of folates. Thus, folic acid and other art-recognized folate receptor-binding ligands can be chemically bonded to polynucleotides, proteins, or other desired exogenous molecules using art-recognized coupling techniques to provide a folate receptor-binding complex which is readily endocytosed into living cells. In accordance with this embodiment of the present invention, a folate/exogenous molecule complex is brought into contact with a membrane having associated folate receptors for a time sufficient to allow binding of the folate moiety of the complex to a corresponding folate receptor. Folate receptor-binding triggers the initiation of cellular processes that result in transmembrane transport of the complex.

The methods of this invention are particularly useful for increasing the internalization efficiency (cellular uptake) of exogenous molecules that are normally resistant to cellular internalization. Proteins and polynucleotides previously recognized as difficult to move across cell membranes can be internalized by a cell through application of the method of the present invention. For example, transformation of target cell lines resulting in expression of a protein product has been accomplished by coupling the desired polynucleotide to either biotin or folates, and contacting the cells with the resulting complex for a time sufficient to promote cellular internalization. In one case, a DNA plasmid containing a gene sequence coding for chloramphenicol acetyltransferase (CAT), was biotinylated and transported into *E. coli* via a biotin receptor mediated endocytotic pathway and expressed. Similar examples of transformation or transfection have been noted for biotin or folate linked nucleic acids in mammalian systems, prokaryotic systems, and plants. The use of biotin and folates complexes to enhance cellular uptake of complexed exogenous molecules has been demonstrated in vivo and in vitro.

DETAILED DESCRIPTION OF THE INVENTION

In accordance with one embodiment of this invention, there is provided a method for enhancing transport of an exogenous molecule across a membrane of a living cell. The method comprises the step of contacting the membrane with the exogenous molecule complexed with a ligand selected from the group consisting of biotin, biotin receptor-binding analogs of biotin, and other biotin receptor-binding ligands, for a time sufficient to permit transmembrane transport of said ligand complex. In a second embodiment, there is provided a method for enhancing transport of an exogenous molecule across a membrane of a living cell, comprising the step of contacting the membrane with the exogenous molecule complexed with a ligand selected from the group consisting of folic acid, folate receptor-binding analogs of folic acid, and other folate receptor-binding ligands, for a time sufficient to permit transmembrane transport of said ligand complex.

The method of the present invention is effective in all living cells that have biotin and/or folate receptors associated with their cellular membranes. The membrane can define an intracellular volume such as the endoplasmic reticulum or other organelles such as mitochondria, or alternatively, the membrane can define the boundary of the cell.

Living cells which can serve as the target for the method of this invention include prokaryotes and eukaryotes, including yeasts, plant cells and animal cells. The present method can be used to modify cellular function of living cells in vitro, i.e., in cell culture, or in vivo, where the cells form part of or otherwise exist in plant tissue or animal tissue. Thus the cells can form, for example, the roots, stalks or leaves of growing plants and the present method can be performed on such plant cells in any manner which promotes contact of the exogenous molecule/folate or biotin complex with the targeted cells having the requisite receptors. Alternatively, the target cells can form part of the tissue in an animal. Thus the target cells can include, for example, the cells lining the alimentary canal, such as the oral and pharyngeal mucosa, the cells forming the villi of the small intestine, or the cells lining the large intestine. Such cells of the alimentary canal can be targeted in accordance with this invention by oral administration of a composition comprising an exogenous molecule complexed with folates or biotin or their receptor-binding analogs. Similarly, cells lining the respiratory system (nasal passages/lungs) of an animal can be targeted by inhalation of the present complexes; dermal/epidermal cells and cells of the vagina and rectum can be targeted by topical application of the present complexes; and cells of internal organs including cells of the placenta and the so-called blood/brain barrier can be targeted particularly by parenteral administration of the present complexes. Pharmaceutical formulations for therapeutic use in accordance with this invention containing effective amounts of the presently described folate and biotin complexes, in admixture with art-recognized excipients appropriate to the contemplated route of administration are within the scope of this invention.

Since not all natural cell membranes possess biologically active biotin or folate receptors, practice of the method of this invention in vitro on a particular cell line can involve altering or otherwise modifying that cell line first to ensure the presence of biologically active biotin or folate receptors. Thus, the number of biotin or folate receptors on a cell membrane can be increased by growing a cell line on biotin or folate deficient substrates to promote biotin and folate receptor production, or by expression of an inserted foreign gene for the protein or apoprotein corresponding to the biotin or folate receptor.

The present invention is utilized to enhance the cellular uptake of exogenous molecules, in particular those molecules capable of modulating or otherwise modifying cell function, including pharmaceutically active compounds or diagnostic agents. Suitable exogenous molecules can include, but are not limited to: peptides, oligopeptides, proteins, apoproteins, glycoproteins, antigens and antibodies thereto, haptens and antibodies thereto, receptors and other membrane proteins, retro-inverso oligopeptides, protein analogs in which at least one non-peptide linkage replaces a peptide linkage, enzymes, coenzymes, enzyme inhibitors, amino acids and their derivatives, hormones, lipids, phospholipids, liposomes; toxins such as aflatoxin, digoxin, xanthotoxin, rubratoxin; antibiotics such as cephalosporins, penicillin, and erythromycin; analgesics such as aspirin, ibuprofen, and acetaminophen, bronchodilators such theophylline and albuterol; beta-blockers such as propranolol, metoprolol, atenolol, labetolol, timolol, penbutolol, and pindolol; antimicrobial agents such as those described above and ciprofloxacin, cinoxacin, and norfloxacin; antihypertensive agents such as clonidine, methyldopa, prazosin, verapamil, nifedipine, captopril, and enalapril; cardiovascular agents including antiarrhythmics, cardiac glycosides, antianginals and vasodilators; central nervous system agents including stimulants, psychotropics, antimanics, and depressants; antiviral agents; antihistamines such as chlorpheniramine and brompheniramine; cancer drugs including chemotherapeutic agents; tranquilizers such as diazepam, chordiazepoxide, oxazepam, alprazolam, and triazolam; anti-depressants such as fluoxetine, amitriptyline, nortriptyline, and imipramine; H-2 antagonists such as nizatidine, cimetidine, famotidine, and ranitidine; anticonvulsants; antinauseants; prostaglandins; muscle relaxants; anti-inflammatory substances; stimulants; decongestants; antiemetics; diuretics; antispasmodics; antiasthmatics; anti-Parkinson agents; expectorants; cough suppressants; mucolytics; vitamins; and mineral and nutritional additives. Other molecules include nucleotides; oligonucleotides; polynucleotides; and their art-recognized and biologically functional analogs and derivatives including, for example; methylated polynucleotides and nucleotide analogs having phosphorothioate linkages; plasmids, cosmids, artificial chromosomes, other nucleic acid vectors; antisense polynucleotides including those substantially complementary to at least one endogenous nucleic acid or those having sequences with a sense opposed to at least portions of selected viral or retroviral genomes; promoters; enhancers; inhibitors; other ligands for regulating gene transcription and translation, and any other biologically active molecule that can form a complex with biotin or folate, or analogs thereof, by direct conjugation of the exogenous molecule with biotin or biotin analog or folate or folate analog through a hydrogen, ionic, or covalent bonding. Also in accordance with this invention is the use of indirect means for associating the exogenous molecule with biotin or folate, or analogs thereof to form ligand complexes, such as by connection through intermediary linkers, spacer arms, bridging molecules, or liposome entrapment, all of which can act to associate the biotin or biotin analog or folate or folate analog with the exogenous molecule of interest. Both direct and indirect means for associating the ligand and the exogenous molecule must not prevent the binding of the ligand held in association with the exogenous molecule to its respective ligand receptor on the cell membrane for operation of the method of the present invention.

Generally, any manner of forming a complex between an exogenous molecule of interest and a ligand capable of triggering receptor mediated endocytosis can be utilized in accordance with the present invention. This can include covalent, ionic, or hydrogen bonding of the ligand to the exogenous molecule, either directly or indirectly via a linking group. The complex is typically formed by covalent bonding of the receptor-activating moiety to the exogenous molecule through the formation of amide, ester or imino bonds between acid, aldehyde, hydroxy, amino, or hydrazo groups on the respective components of the complex. Art-recognized biologically labile covalent linkages such as imino bonds (—C=N—) and so-called "active" esters having the linkage —COOCH$_2$O— or —COOCH(CH$_3$)O— are preferred, especially where the exogenous molecule is found to have reduced functionality in the complexed form. Hydrogen bonding, e.g., that occurring between complementary strands of nucleic acids, can also be used for complex formation. Thus a biotinylated or folated oligonucleotide complementary to at least a portion of a nucleic acid to be delivered to a cell in accordance with this invention can be hybridized with said nucleic acid and the hybrid (complex) used per this invention to enhance delivery of the nucleic acid into cells.

Because of the ready availability of biotinylating reagents and biotinylating methods suitable for use with peptides, proteins, oligonucleotides, polynucleotides, lipids, phospholipids, carbohydrates, liposomes or other lipid vesicles, lower molecular weight therapeutic agents, bioactive compounds, and carriers for therapeutic agents, biotin is a preferred complex forming ligand for use in carrying out this invention. Generally, the biotin/exogenous molecule complex is formed by covalently binding biotin or a biotin derivative to the exogenous molecule of interest. Transmembrane transport via the biotin/biotin receptor pathway is also preferred because biotin is a necessary nutrient for a wide variety of cells, and biotin receptors that mediate endocytotic activity have been identified in mammalian, plant, and bacterial cells.

Formation of a complex between biotin and an exogenous molecule of interest is readily accomplished. Biotin and its analogs can be easily conjugated to proteins by activating the carboxyl group of biotin, thereby making it reactive with the free amino groups of the proteins to form a covalent amide linking bond. A biotinylating reagent such as D-biotin-N-hydroxy-succinimide ester or biotinyl-p-nitrophenyl ester can be used. The activated ester reacts under mild conditions with amino groups to incorporate a biotin residue into the desired molecule. The procedure to be followed for biotinylating macromolecules using D-biotin-N-hydroxy-succinimide ester is well known in the art (Hofmann et al., *J.Am.Chem.Soc.* 100, 3585–3590 (1978)). Procedures suitable for biotinylating an exogenous molecule using biotinyl-p-nitrophenyl ester as a biotinylating reagent are also well known in the art (Bodanszk et al., *J.Am.Chem-.Soc.* 99, 235 (1977)). Other reagents such as D-biotinyl-ε-aminocaproic acid N-hydroxy-succinimide ester in which ε-aminocaproic acid serves as a spacer link to reduce steric hindrance can also be used for the purposes of the present invention.

Oligonucleotides and polynucleotides can also be biotinylated using both indirect and direct methods. Indirect methods include end-labeling of a polynucleotide with a biotinylated nucleotide, or nick translation that incorporates biotinylated nucleotides. Nick translation or end labeling of DNA can be accomplished using methods described in Maniatis et al., *Molecular Cloning: A Laboratory Manual*, pp. 109–116, Cold Spring Harbor Press (1982). Direct methods are those procedures in which biotin is directly attached to a target polynucleotide using a biotinylating reagent. Photoactivatible reagents such as the acetate salt of N-(4-azido-2-nitrophenyl)-N-(3-biotinylaminopropyl)-N-methyl-1,3-propanediamine (photobiotin) can be used to biotinylate DNA according to the method of Forster et al., *Nuc. Acids Res.* 13:745–761. An alternative method uses a biotin hydrazide reagent in a bisulfite catalyzed reaction capable of transamination of nucleotide bases such as cytidine according to the method described by Reisfeld et al., *B.B.R.C.* 142:519–526 (1988). This method simply requires a 24 hour incubation of DNA or RNA with biotin hydrazide at 10 mg/ml in an acetate buffer, pH 4.5, containing 1M bisulfite. Biotin hydrazide can also be used to biotinylate carbohydrates or other exogenous molecules containing a free aldehyde.

Biotin analogs such as biocytin, biotin sulfoxide, oxybiotin and other biotin receptor-binding compounds are liquids that may also be used as suitable complexing agents to promote the transmembrane transport of exogenous molecules in accordance with this invention. Other compounds capable of binding to biotin receptors to initiate receptor mediated endocytotic transport of the complex are also contemplated. Such can include other receptor-binding ligands such as, for example, anti-idiotypic antibodies to the biotin receptor. An exogenous molecule complexed with an anti-idiotypic antibody to a biotin receptor could be used to trigger transmembrane transport of the complex in accordance with the present invention.

Folate receptors that mediate endocytic activity have previously been identified in bacterial cells (Kumar et al., *J. Biol. Chem.*, 262, 7171–79 (1987)). Folic acid, folinic acid, pteropolyglutamic acid, and folate receptor-binding pteridines such as tetrahydropterins, dihydrofolates, tetrahydrofolates, and their deaza and dideaza analogs are preferred complex-forming ligands used in accordance with a second embodiment of this invention. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid derivatives are conventionally termed "folates", reflecting their capacity to bind with folate-receptors, and such ligands when complexed with exogenous molecules are effective to enhance transmembrane transport. Other folates useful as complex forming ligands for this invention are the folate receptor-binding analogs aminopterin, amethopterin (methotrexate), $N^{10}$-methylfolate, 2-deaminohydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). Other suitable ligands capable of binding to folate receptors to initiate receptor mediated endocytotic transport of the complex include anti-idiotypic antibodies to the folate receptor. An exogenous molecule in complex with an anti-idiotypic antibody to a folate receptor is used to trigger transmembrane transport of the complex in accordance with the present invention.

Folated ligands can be complexed with the exogenous molecules hereinbefore defined using art-recognized covalent coupling techniques identical to or closely paralleling those referenced above for the biotinylate ligand complexes. Thus, for example, a carboxylic acid on the folate moiety or on the exogenous molecule can be activated using, for example, carbonyldiimidazole or standard carbodiimide coupling reagents such as 1-ethyl-3-(3-dimethylaminopropyl)carbodiimide (EDC) and thereafter reacted with the other component of the complex having at least one nucleophilic group, viz hydroxy, amino, hydrazo, or thiol, to form the respective complex coupled through an ester, amide, or thioester bond. Thus complexes can be readily formed between folate ligands and peptides, proteins, nucleic acids, including both RNA and DNA, phosphorodithioate analogs of nucleic acids, oligonucleotides, polynucleotides, lipids and lipid vesicles, phospholipids, carbohydrates and like exogenous molecules capable of modifying cell function. The ligand complexes enable rapid, efficient delivery of the cell function-modifying moiety through cellular membranes and into the cell.

It is contemplated that both folate and biotinylate-receptor binding ligands can be used advantageously in combination to deliver exogenous molecules through cell membranes. Thus, for example, an exogenous molecule can be multiply conjugated with both folate and biotinylate ligands to enhance opportunity for binding with the respective cell membrane receptors. Alternatively, independent portions of a dose of an exogenous compound can be biotinylated and folate-coupled, respectively, and the portions of the resulting complexes can subsequently be combined to provide a mixture of ligand complexes for modification of cell function.

Receptor mediated cellular uptake of biotinylated or folate-derivatized polynucleotides provides a convenient, efficient mechanism for transformation of cells. The method is particularly valuable for cell transformation because it is applicable even to cell types, such as plant cells, which are normally resistant to standard transformation techniques. Delivery of foreign genes to the cell cytoplasm can be accomplished with high efficiency using the present invention. Once delivered through the cell membrane to the cell interior, foreign genes can be expressed to produce a desired protein. In addition, other nucleic acids can be introduced, for example, an antisense-RNA sequence capable of binding interference with endogenous messenger RNA.

Artificially generated phospholipid vesicles have been used as carriers for introducing membrane-impermeable substances into cells, as instruments for altering lipid composition of membranes in intact cells, and as inducers of cell fusion. Liposome/cell membrane interaction is potentiated in accordance with one application of the method of this invention by contacting the cell membrane with a liposome containing the exogenous molecule and bearing ligands on its membrane contacting surface. For example, liposome-forming phospholipids can be biotinylated or folate-conjugated through, for example, headgroup functional groups such as hydroxy and amino groups. The resulting phospholipid/ligand complex is then used itself or in combination with unmodified phospholipids to form liposomes containing exogenous molecules capable of modulating or otherwise modifying cell function. The resulting liposomes, again formed in whole or in part from the phospholipid/biotin or folate complex, present biotin or folate receptor-binding groups to the cell surface, triggering the receptor mediated endocytosis mechanism, thereby promoting delivery of the liposome-contained substances into the cell. One readily available phospholipid that can be used in accordance with the above-described method is phosphatidylethanolamine. That phospholipid can be conveniently complexed using art-recognized procedures with either biotin, biotin analogs or folate-receptor-binding ligands to form a phospholipid/ligand complex. The receptor-binding complex can be combined with other phospholipids, for example, phosphatidylcholine and that mixture can be used to form liposomes containing biologically active substances for delivery of those biologically active substances to cells.

It is further contemplated in accordance with this invention that other cell nutrients for which there exists receptors and associated receptor mediated endocytotic uptake could serve as ligands for forming complexes with exogenous molecules to enhance their cellular uptake. Among nutrients believed to trigger receptor mediated endocytosis and having application in accordance with the presently disclosed method are niacin, pantothenic acid, riboflavin, thiamin, pyridoxal, and ascorbic acid. These non-organometallic nutrients, and their analogs and derivatives thereof, constitute ligands that can be coupled with exogenous molecules to form ligand complexes for contact with cell membranes following the same procedures described hereinabove for biotin and folate. These foregoing nutrients are generally required nutrients for mammalian cells. Exogenous molecules coupled with the foregoing non-organometallic nutrients can be used to deliver effective amounts of therapeutic agents or pharmaceutically active agents such as previously described through parenteral or oral routes of administration to human or animal hosts.

The following examples are provided to illustrate further the method of the present invention.

EXAMPLE 1

RAT PHEOCHROMOCYTOMA CELL UPTAKE OF BIOTIN CONJUGATED INSULIN

Rat pheochromocytoma (PC-12) cells were obtained from America Type Culture Collection and were grown (37° C., 5% $CO_2$ in humidified air) attached to plastic flasks for 2 to 3 weeks until confluent in a medium of 85% RMPI 1640, 10% v/v heat inactivated horse serum, and 5% fetal calf serum containing 1% streptomycin-penicillin.

Biotin and fluorescein labeled insulin was prepared. To 1 ml of a 1 mg/ml solution of insulin protein in phosphate buffered saline was added simultaneously 100 µl of a 1 mg/ml solution of fluorescein isothiocyanate (FITC) in dimethylformamide (DMF) and 100 µl of a 1 mg/ml solution of N-hydroxysuccinimido biotin in dimethylsulfoxide (DMSO). The two labeling reagents were allowed to react at room temperature for 4 hours, after which the unreacted reagents were quenched with 10 µl ethanolamine. The quenched reaction mixture was then dialyzed against double distilled water until unreacted fluorescein derivatives no longer dialyzed into the water. The covalent attachment of biotin and fluorescein to the desired protein was confirmed by sodium dodecyl sulfate-polyacrylamide gel electrophoresis and western blot analysis.

As a control, non-biotinylated fluorescein labeled insulin was prepared. 1 ml of a 1 mg/ml solution of insulin was added 0.5 ml of a 1 mg/ml solution of fluorescein isothiocyanate (FITC) in dimethylformamide (DMF). The reaction was allowed to proceed for 4 hours in the dark at room temperature. After 4 hours the reaction was quenched with 10 µl ethanolamine, and the labeled insulin solution was dialyzed against double distilled water until unreacted FITC no longer appeared in the solution.

The rat PC12 cells were grown in modified RMPI 1640 medium as a monolayer on the bottom of a culture flask. Before removing the cells, the monolayer was washed with a 20 ml portion of fresh Locke's solution. The cells were then displaced into 20 ml of the Locke's solution by gentle agitation with a stream Locke's solution. The suspended cells were pelleted by centrifugation at 10,000×g for 10 seconds and after resuspending in Locke's solution in separate polycarbonate tubes (40 ml/tube) to a final density of $1.14 \times 10^6$ cells/ml, the following amounts of proteins were added to the cell suspensions: 40 µg fluorescein-labeled insulin was added to the first tube, and to the control tube was added 40 µg biotin-conjugated insulin labelled with fluorescein. The tubes were allowed to incubate at 37° C. At intervals of 5, 15 and 33 minutes, 0.5 ml of each cell suspension was removed and pelleted at 10,000×g for 10 seconds. The cell pellet was washed and repelleted twice in 1 ml Locke's solution and then fixed by addition of 200 µl of a 2% formalin solution in phosphate buffered saline. Thirteen microliters of the fixed cell suspension was then added to a microscope slide and viewed with the fluorescent microscope to detect internalized proteins. No evidence of internalization was noted for the fluorescein labelled insulin acting as a control. Cellular internalization was indicated for the biotinylated insulin labelled with fluorescein, with the amount internalized increasing with time.

EXAMPLE 2

RAT PHEOCHROMOCYTOMA CELL UPTAKE OF BIOTIN CONJUGATED HEMOGLOBIN

Following the same general procedure set forth in Example 1 hemoglobin was biotinylated, and the biotinylated form was shown to be preferentially internalized by rat pheochromocytoma cells as compared to non-biotinylated hemoglobin.

EXAMPLE 3

SOYBEAN CELL UPTAKE OF BOVINE SERUM ALBUMIN

Soybean cell suspension cultures of Glycine max Merr Var Kent were maintained by transferring cells to fresh W-38 growth medium every 7 days.

To 20 ml of a suspension culture of soybean cells was added 10 µg of either fluorescein-labeled (control) or fluorescein and biotin labelled bovine serum albumin. The cells were allowed to incubate for up to 6 hours. At varying time intervals 1 ml of the cell suspension was filtered to remove the growth medium, washed with 50 ml fresh growth medium, and resuspended in 20 ml of the same medium. The cell suspension was then viewed with a fluorescent microscope to determine whether cellular internalization of the labelled bovine serum albumin had occurred. Cellular internalization was indicated only for biotinylated bovine serum albumin.

EXAMPLE 4

SOYBEAN CELL UPTAKE OF INSULIN

Following the same general procedure set forth in Example 3 insulin was biotinylated, and the biotinylated form of insulin was shown to be preferentially internalized by soybean cells as compared to non-biotinylated insulin.

EXAMPLE 5

SOYBEAN CELL UPTAKE OF HEMOGLOBIN

Following the same general procedure set forth in Example 3 hemoglobin was biotinylated, and the biotinylated form of hemoglobin was shown to be preferentially internalized by soybean cells as compared to non-biotinylated hemoglobin.

EXAMPLE 6

CARROT CELL UPTAKE OF BOVINE SERUM ALBUMIN

Carrot cells of wild type origin were established and maintained in MS growth medium supplemented with 0.1 mg/L 2,4-dichlorophenoxyacetic acid. Bovine serum albumin was labelled with fluorescein alone as a control or with fluorescein and biotin following the procedures detailed in Example 3. The carrot cells were then incubated in the presence of the respective labelled bovine serum albumin for 7 hours. All other conditions were the same as those described in Example 3 above. Cellular internalization was found only in those cells contacted with biotin labelled bovine serum albumin.

EXAMPLE 7

CARROT CELL UPTAKE OF INSULIN

Following the same general procedure set forth in Example 6 insulin was biotinylated, and the biotinylated form was shown to be preferentially internalized by carrot cells as compared to non-biotinylated insulin.

EXAMPLE 8

CARROT CELL UPTAKE OF HEMOGLOBIN

Following the same general procedure set forth in Example 6 hemoglobin was biotinylated, and the biotinylated form was shown to be preferentially internalized by carrot cells as compared to non-biotinylated hemoglobin.

EXAMPLE 9

SOYBEAN CELL DEGRADATION OF HEMOGLOBIN

To determine whether hemoglobin was rapidly degraded following cellular internalization by transmembrane transport, soybean cells were allowed to internalize and metabolize biotinylated hemoglobin for a period of 8 hours under conditions described in Example 5, after which the soybean cells were rapidly homogenized in a sodium dodecyl sulfate solution to disaggregate and denature all protein material. The solubilized polypeptides were separated according to molecular weight by polyacrylamide gel electrophoresis and then electroblotted onto nitrocellulose paper. The positions of the biotin-labeled peptides were then visualized on the nitrocellulose blot by staining with horseradish peroxidase-linked avidin and the colored substrate, p-chloronaphthol. All of the biotin-linked material was found to migrate with an apparent molecular weight of ~16,000 daltons, about equal to the molecular weight of the parent globin chains of hemoglobin, indicating no breakdown of the parent globin chains had occurred during the 8 hour incubation period.

EXAMPLE 10

IN VIVO DELIVERY TO MICE OF SOYBEAN TRYPSIN INHIBITOR

Soybean trypsin inhibitor (SBTI) (~6 mg) was labeled with radioactive $^{125}$I using 8 iodobeads (Bio Rad) in 1 mL buffer which was then dialyzed to remove unreacted $^{125}$I. After dividing into two equal fractions, one fraction was biotinylated with N-hydroxysuccinimidyl biotin and the other fraction was left as an unmodified control. Mice (~25 g) were then injected with either the biotinylated SBTI or the control SBTI by insertion of a hypodermic syringe containing a 25 gauge needle into the tail vein of the mouse. After 15 minutes, each mouse was sacrificed and then perfused with heparin-containing isotonic saline via the direct cardiac influx and efflux method. When the various tissues appeared to be blood-free, the perfusion was terminated and each tissue/organ was removed, weighed, and counted for $^{125}$I-SBTI in a gamma counter. Although some radioactivity was detected in the mice treated with non-biotinylated $^{125}$I-SBTI, between 4 and 100 times more $^{125}$I-SBTI was found in the mice treated with biotinylated SBTI, indicating successful in vivo delivery to murine cellular tissue.

| | Counts per minute/gram wet weight | |
| --- | --- | --- |
| Tissue | Control SBTI | Biotin SBTI |
| Liver | 535 | 1967 |
| Lung | 107 | 2941 |
| Kidney | 5152 | 8697 |
| Intestine | 0 | 700 |
| Muscle | 0 | 1065 |
| Heart | 0 | 739 |
| Brain | 0 | 267 |

EXAMPLE 11

SOYBEAN CELL UPTAKE OF SALMON SPERM DNA

Protein free salmon-sperm DNA, either in a highly polymerized form ($\geq 50,000$ base pair length) or in a sheared form ($\leq 500$ base pair length), was transaminated at the cytosine residues. The transaminated DNA (1 mg) was labeled with fluorescein via the addition of 0.5 mg of fluorescein isothiocyanate (FITC) in dimethylsulfoxide (DMSO). The resulting reaction mixture was divided into two portions and the labeling reaction was quenched in one portion by addition of 10 μL of ethanolamine. This quenched portion served as the non-biotinylated control. The remaining DNA was then covalently labeled with biotin via reaction with 0.5 mg of N-hydroxysuccinimidyl biotin in DMSO. After purification, the two derivatives (1 μg/ml) were separately incubated with soybean suspension culture cells at room temperature for 6 hours and then the cells were washed with 50 ml fresh growth medium and observed by fluorescence microscopy. Only the biotinylated DNA entered the soybean cells.

EXAMPLE 12

E. COLI TRANSFORMATION AND EXPRESSION OF AMPICILLIN RESISTANT GENE

Plasmid DNA (pUC8) was biotinylated via nick translation in the presence of biotin-14-dATP using a commercially available nick translation kit (Bethesda Research Laboratories). The biotinylated DNA and unmodified DNA (1 μg) were added to E. coli strain Cu 1230 that had been made competent by treatment with MgCl$_2$ and CaCl$_2$ following the method of Maniatis et al., *Molecular Cloning: A Laboratory Manual*, pp. 250–251, Cold Spring Harbor Press (1987). After transformation, the successful transformants were selected by plating cells on LB media which contained 50 μg/ml ampicillin and then incubated overnight at 37° C. Colonies which survived the ampicillin were counted and the transformation efficiency was determined. The number of surviving E. coli colonies was at least 100-fold greater in E. coli transformed with the biotinylated plasmids.

EXAMPLE 13

BLOCKADE OF DELIVERY OF BIOTINYLATED PROTEINS INTO SOYBEAN CELLS BY COMPETITION WITH UNLIGATED BIOTIN

Insulin, ribonuclease (RNase) and bovine serum albumin (BAS) were individually biotinylated following the same general procedure set forth in Example 1 above. A sample of each of the biotinylated proteins and an unmodified sample of the same protein (control protein) were radioiodinated according to the following protocol. To 1 mL of a 200 mM phosphate buffer, pH 7.0, containing 3 iodobeads (Pierce Chemical Co.) was added 0.2 mCi [$^{125}$I]-NaI (carrier-free in 1 n NaOH, Amersham) and the mixture was allowed to incubate for 5 minutes to liberate the active iodine species, according to the supplier's instructions. After activation, 1 mg of desired biotinylated or control protein was added in 0.5 mL of iodination buffer. The iodination was allowed to proceed with stirring for 20 minutes. After the iodination was complete, the product was isolated via gel filtration on a Biogel PH-10 column. Typical iodinations of ribonuclease A (Sigma Chemical Co.) yielded a product emitting $2\times10^5$ cpm/μg.

Uptake of $^{125}$I-labeled proteins by soybean suspension culture cells in the early exponential growth phase was then assayed as follows. To each culture was added sufficient $^{125}$I-labeled macromolecule to achieve a final concentration of 10 μg/mL, and the suspension was incubated at 23° for the desired time. After the desired incubation period, the cells were washed for 5 minutes in growth media rebuffered to pH 8 with 15 mM glycylglycine to remove surface bound ligand. The cell suspension was then filtered, washed with 200 volumes growth media, and placed in counting vials.

Uptake of biotin-conjugated RNase was rapid, reaching $6\times10^6$ molecules internalized per cell in the first 3 hours. In contrast, unmodified RNase was not internalized, demonstrating the importance of the biotin adduct. To further confirm the role of biotin in mediating the delivery of RNase, the cell suspension was treated with 1 mM free biotin directly prior to addition of the biotin-derivatized RNase. Free biotin competitively blocked delivery of the conjugated protein into the soybean cells. Therefore, it can be concluded that the internalization process involves recognition of biotin by a limited number of receptors on the plant cell surface.

Similar studies with biotin-labeled BSA and insulin yielded virtually identical results.

EXAMPLE 14

PARTIAL PURIFICATION OF BOVINE SERUM ALBUMIN FOLLOWING ITS INTERNALIZATION BY CULTURED SOYBEAN CELLS

Radiolabeled, biotinylated bovine serum albumin was allowed to bind and enter cultured soybean cells following the same general procedure set forth in Example 13, after which the cells were thoroughly washed, homogenized and extracted to remove cytoplasmic soluble proteins. This cytoplasmic protein extract was separated using standard chromatographic techniques on a Sephadex G-25 gel filtration column to determine whether any small molecular weight fragments might be generated during the co-delivery process. Comparison of the elution profile of the $^{125}$I-labeled material isolated from the cell extract with the profile of unmodified $^{125}$I-serum albumin showed that the majority of the internalized protein remained intact throughout the 2 hour duration of the internalization study.

EXAMPLE 15

RESTORATION OF GROWTH IN CULTURED CELLS DEFICIENT IN HYPOXANTHINE-GUANINE PHOSPHORIBOSYL TRANSFERASE (HGPRT) UPON ADDITION OF BIOTINYLATED-HGPRT

Cells deficient in HGPRT (i.e., the defect in Lesch-Nyhan Syndrome) are able to grow only in a cellular growth medium containing hypoxanthine, aminopterin and thymidine, (HAT), supplemented with purines. However, these same cells were found to grow normally in HAT medium after internalization of biotin-linked HGPRT via the biotin-mediated endocytosis pathway. HGPRT was biotinylated in the presence of hypoxanthine and phosphoribosyl pyrophosphate (to protect the active site) with N-hydroxysuccinimido biotin. The crosslinked enzyme retained 55% of the original activity and SDS PAGE analysis followed by transblotting and avidin-peroxidase binding indicated that a 1–4 biotins were attached per molecules of HGPRT. HGPRT deficient fibroblasts (GM 00152) incubated with biotinylated HGPRT ($4.6\times10^4$ units/cell) grew at a rate comparable to cells supplemented with purines for at least 24 hours. Appropriate control incubations did not grow on HAT medium supplemented with HGPRT, biotin, phosphoribosyl, and inosine monophosphate.

EXAMPLE 16

TRANSFORMATION OF CULTURED SOYBEAN CELLS WITH A KANAMYCIN RESISTANCE GENE USING THE BIOTIN DELIVERY SYSTEM

The expression vector pGA642–643 containing a bacterial kanamycin resistance gene was nicked with EcoRl and the sticky ends were filled in using biotinylated ATP and a T4 polymerase-based nick translation kit following the general procedure set forth in Example 12. Identical control plasmids were left unmodified. Then, to 40 ml of a soybean cell suspension was added either the biotinylated plasmid or the control (nonbiotinylated) plasmid. After incubation for 10 hours, the cells from each flask were transferred to fresh growth medium containing 100 μg/ml kanamycin and allowed to proliferate under normal conditions. Each flask was also transferred to fresh medium containing 100 μg/ml kanamycin every 3 days. By day 10, the flask treated with the biotinylated plasmid had increased ~6-fold in cell mass, while the flask treated with the control plasmid exhibited no measurable growth.

EXAMPLE 17

USE OF FOLIC ACID CONJUGATION TO DELIVER RIBONUCLEASE INTO CULTURED HUMAN CELLS

Activated folic acid was prepared by dissolving 1 mg of folic acid and 3.8 equivalents of 1-ethyl-3-(3-dimethylaminopropyl) carbodiimide (EDC) in 0.5 ml of dimethylsulfoxide (DMSO). The solution was allowed to set for 2.5 hours. A sample of folate-labeled bovine ribonuclease was prepared by treating the ribonuclease with ~34-fold molar excess of EDC-activated folate. The resulting derivatized RNase contained 12–14 covalently bound folates per protein molecule. A second sample of the ribonuclease was left unmodified to serve as a control. The folate-labeled sample and the control sample were radioiodinated following the same general procedure set forth in Example 13. Following exhaustive dialysis, the two $^{125}$I-labeled samples were added to KB cells (a human nasopharyngeal cell line) and examined for uptake of $^{125}$I-RNase after 30 minutes. No protein uptake was seen for RNase control samples, while $10^7$ molecules per cell were internalized by the RNase labeled with folate (RNase-Folate). To confirm that the uptake was indeed folate-mediated, the KB cells were treated with either control RNase or folate-labeled RNase in the presence of a 100-fold molar excess of unligated folate (100X). The control RNase again displayed no internalization; uptake of the RNase-Folate conjugate was reduced ~7-fold by competitive inhibition. Similar studies yielded corresponding results using human HeLa cells.

EXAMPLE 18

USE OF FOLIC ACID CONJUGATION TO DELIVER SOYBEAN TRYPSIN INHIBITOR (SBTI) INTO CULTURED HUMAN CELLS

Experiments following the general procedure set forth in Example 17, with soybean trypsin inhibitor being substituted for ribonuclease, were conducted with virtually identical results. Folate ligation was again demonstrated to be essential for uptake of SBTI by KB cells.

EXAMPLE 19

VISUALIZATION OF RIBONUCLEASE ENDOCYTOSIS BY KB CELLS USING A CONFOCAL MICROSCOPE

Bovine ribonuclease (RNase) was labeled with fluorescein isothiocyanate following the same general procedure set forth in Example 1 and then further labeled with folate following the same general procedure set forth in Example 17. RNase labeled only with fluoroscein was used as a control. Following extensive dialysis against growth medium, the control and folate-labeled RNase samples were added to separate cultures of KB cells. After 60 minute incubation, the cells were thoroughly washed and examined for uptake. Only the folate-labeled samples displayed any internal fluorescence when viewed with laser excitation under the confocal microscope (Bio Rad). Furthermore, using the confocal's capability of focusing on a single horizontal plane in each cultured cell, it was readily evident that vesicles filled with the fluorescent-labeled, folate-bound ribonuclease were forming on all regions of the cell surface, pinching off via endocytosis into the interior, and entering the cytoplasm. The vesicles, measuring 0.8 to 1.0 μm across, were easily large enough to accommodate large biomolecules such as proteins and DNA plasmids.

EXAMPLE 20

UPTAKE OF RIBONUCLEASE IN COMPLEX WITH FOLATE BY WHITE BLOOD CELLS

Fluorescein-labeled RNase was either conjugated to folate or left unmodified (control) following the same general procedure set forth in Example 19. The folate-conjugated and control samples were then added to freshly drawn whole human blood, incubated at 37° C. for 2 hours and then washed thoroughly and examined under the fluorescence microscope. Cells bearing folate receptors that were brought into contact with the RNase/folate/fluorescein complex were found to fluoresce. None of the control cells exhibited fluorescence.

EXAMPLE 21

IN VIVO DELIVERY OF RIBONUCLEASE THROUGHOUT TISSUES OF LIVE MICE FOLLOWING INTRAVENOUS INJECTION

Ribonuclease was labeled with $^{125}$I following the same general procedure set forth in Example 13 and then further conjugated with folate or left unmodified to serve as a control, following the general procedure set forth in Example 17. Live mice were injected with either the folate-conjugated or control sample by inserting a 27 gauge needle into the tail vein of the mice and injecting 0.2 ml of the appropriate sample dissolved in physiological saline. After 1 hour, the mice were anesthetized, perfused with saline and dissected to determine the specific radioactivity of each organ, following the general procedure set forth in Example 10. Uptake was determined by relative comparison of specific radioactivity of the various tissues examined (units compared were counts per minute/gram of tissue divided by the specific activity of a blood sample drawn 3 minutes after injection, i.e., in order to normalize for any variability in the amount injected). Folate conjugation provided greatly enhanced uptake by the liver and lung, while the kidney, an organ responsible for clearance of unwanted proteins, was enriched in unmodified RNase.

Similar results were obtained when the mice were allowed to live for 18 hours post-injection, with preferential uptake of folate-conjugated RNase also being noted in the intestine, heart, muscle and brain.

EXAMPLE 22

IN VIVO DELIVERY OF RIBONUCLEASE THROUGHOUT TISSUES OF LIVE MICE FOLLOWING INTRAPERITONEAL INJECTION

Folate-derivatized and control RNase ($^{125}$ I-labeled) were prepared as described in Example 21 and injected into the peritoneal cavity of 30 g mice using a 27 gauge needle and syringe. After 17 hours, the mice were anesthetized, perfused, and dissected to remove various body tissues. Each tissue was then weighted and counted for radioactivity. The specific uptake of both the control and folate-conjugated RNase were compared following the general procedure set forth in Example 21. As compared to intravenous administration, intraperitoneal injection resulted in enhanced delivery of the folate-derivatized RNase to all tissues except the kidney. Transmembrane delivery across the blood/brain barrier was demonstrated by the brain tissue's preferential uptake of the folate-labeled protein. Similar results were obtained in two other repetitions of the foregoing procedure.

EXAMPLE 23

REVERSION OF src-TRANSFORMED FIBROBLASTS TO DIFFERENTIATED STATE UPON TREATMENT WITH ANTI-SENSE DNA CONJUGATED TO FOLATE A pentadecameric oligonucleotide DNA probe of the formula

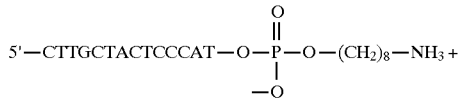

complementary to a sequence spanning the initiation codon of the Rous sarcoma src oncogene and containing a free 3' amino group was derivatized with folate using carbodiimide chemistry. A second sample was left unmodified as a control. Both samples were dissolved in phosphate buffered saline and introduced into culture dishes containing fibroblasts transformed by the Rous sarcoma virus (XC cells) at a final oligonucleotide concentration of $8 \times 10^{-6}$M. After 24 hours, the cultured cells were viewed under a microscope. Results showed that ~40% of the cells treated with the folate/antisense oligonucleotide complex had reverted to the normal fibroblast-like morphology, while only ~10% of the controls displayed the same non-transformed phenotype. The remaining cells in both culture dishes retained their highly rounded shape characteristic of the neoplastic state.

What is claimed is:

1. A method of targeting a diagnostic agent for delivery to a folate receptor-bearing cell of an animal, said method comprising the step of administering to said animal a composition comprising a diagnostic agent complexed with a targeting ligand selected from the group consisting of folate, folate receptor-binding analogs of folate, and other folate receptor-binding ligands.

2. The method of claim 1 wherein the diagnostic agent is complexed to the targeting ligand indirectly through a linker.

3. The method of claim 1 wherein the diagnostic agent is contained in a liposome, said liposome comprising liposome-forming phospholipids, at least a portion of which are covalently bound through their headgroups to the targeting ligand.

4. The method of claim 1 wherein the composition is administered parenterally to a vertebrate host.

5. The method of claim 1 wherein the composition is administered orally to a vertebrate host.

6. A method of targeting a diagnostic agent for delivery to a folate receptor-bearing cell of an animal, said method comprising the step of administering to said animal a composition comprising a diagnostic agent complexed with a targeting ligand selected from the group consisting of folate and folate receptor-binding analogs of folate.

7. The method of claim 6 wherein the diagnostic agent is complexed to the targeting ligand indirectly through a linker.

8. The method of claim 6 wherein the diagnostic agent is contained in a liposome, said liposome comprising liposome-forming phospholipids, at least a portion of which are covalently bound through their headgroups to the targeting ligand.

9. The method of claim 6 wherein the composition is administered parenterally to a vertebrate host.

10. The method of claim 6 wherein the composition is administered orally to a vertebrate host.

* * * * *